(12) United States Patent
Lietzau et al.

(10) Patent No.: US 8,012,547 B2
(45) Date of Patent: *Sep. 6, 2011

(54) PYRIDINE COMPOUNDS FOR LIQUID-CRYSTALLINE MIXTURES

(75) Inventors: Lars Lietzau, Darmstadt (DE); Markus Czanta, Darmstadt (DE)

(73) Assignee: Merch Patent GmbH, Darmstadt (DE)

( * ) Notice: Subject to any disclaimer, the term of this patent is extended or adjusted under 35 U.S.C. 154(b) by 5 days.

This patent is subject to a terminal disclaimer.

(21) Appl. No.: 12/597,190

(22) PCT Filed: Apr. 1, 2008

(86) PCT No.: PCT/EP2008/002582
§ 371 (c)(1), (2), (4) Date: Oct. 23, 2009

(87) PCT Pub. No.: WO2008/128622
PCT Pub. Date: Oct. 30, 2008

(65) Prior Publication Data
US 2010/0127212 A1    May 27, 2010

(30) Foreign Application Priority Data
Apr. 24, 2007   (DE) .......................... 10 2007 019 670

(51) Int. Cl.
C09K 19/34 (2006.01)
C07D 211/72 (2006.01)
C07D 211/84 (2006.01)
C07D 211/90 (2006.01)
C07D 405/04 (2006.01)
C07D 405/06 (2006.01)

(52) U.S. Cl. .................. 428/1.1; 252/299.61; 546/282.1; 546/282.4; 546/326; 546/339; 546/345; 546/346

(58) Field of Classification Search ............. 252/299.61; 546/282.1, 282.4, 326, 339, 345, 346; 428/1.1
See application file for complete search history.

(56) References Cited

U.S. PATENT DOCUMENTS

| 5,445,763 A | 8/1995 | Schlosser et al. |
| 5,728,319 A | 3/1998 | Matsui et al. |
| 5,792,386 A | 8/1998 | Matsui et al. |
| 5,858,270 A | 1/1999 | Matsui et al. |
| 7,074,462 B1 | 7/2006 | Bremer et al. |
| 7,531,106 B2 * | 5/2009 | Kirsch et al. ............. 252/299.01 |
| 7,767,277 B2 * | 8/2010 | Lietzau et al. ................. 428/1.1 |
| 2006/0286308 A1 | 12/2006 | Kirsch et al. |
| 2008/0132716 A1 | 6/2008 | Lietzau et al. |
| 2010/0127213 A1 * | 5/2010 | Czanta et al. ............ 252/299.61 |
| 2010/0237285 A1 * | 9/2010 | Lietzau et al. ............. 252/299.6 |

FOREIGN PATENT DOCUMENTS

| DE | 199 49 333 A1 | 4/2001 |
| EP | 0 786 445 A1 | 7/1997 |
| EP | 1 900 792 A1 | 3/2008 |
| WO | WO 2005/019378 A1 | 3/2005 |
| WO | WO 2008/019743 A1 | 2/2008 |

OTHER PUBLICATIONS

International Search Report of PCT/EP2008/002582 (Oct. 13, 2008).
M. Bremer, "Liquid Crystals Based on 2-Fluoropyrimidine and -pyridine: Synthesis, Dielectric Anisotropy and Phase Behavior", Advanced Materials, vol. 7, No. 9 (Sep. 1995) pp. 803-807.
A.I. Pavluchenko et al., "Liquid Crystalline 2,5-Disubstituted Pyridine Derivatives", Liquid Crystals, vol. 19, No. 6 (Dec. 1995) pp. 811-821.

* cited by examiner

*Primary Examiner* — Shean C Wu
(74) *Attorney, Agent, or Firm* — Millen, White, Zelano & Branigan, P.C.

(57) ABSTRACT

The invention relates to liquid-crystalline compounds of the formula I

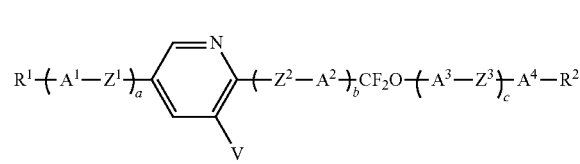

in which
$R^1$, $R^2$, $A^1$, $A^2$, $A^3$, $A^4$, $Z^1$, $Z^2$, $Z^3$, V, a, b and c have the meanings indicated in claim 1, and to liquid-crystalline media comprising at least one compound of the formula I and to electro-optical displays containing a liquid-crystalline medium of this type.

12 Claims, No Drawings

PYRIDINE COMPOUNDS FOR LIQUID-CRYSTALLINE MIXTURES

The invention relates to 2,5-substituted pyridine derivatives and 3-fluoropyridine derivatives containing a difluoromethyleneoxy group and to the use thereof as component(s) in liquid-crystalline media. In addition, the present invention relates to liquid-crystal and electro-optical display elements which contain the liquid-crystalline media according to the invention. The compounds according to the invention contain a difluoromethyleneoxy group in a certain arrangement.

In the preceding years, the areas of application of liquid-crystalline compounds have been considerably broadened to various types of display device, electro-optical devices, electronic components, sensors, etc. For this reason, a number of different structures have been proposed, in particular in the area of nematic liquid crystals. The nematic liquid-crystal mixtures have to date found the broadest application in flat display devices. They have been employed, in particular, in passive TN or STN matrix displays or systems having a TFT active matrix.

The compounds according to the invention can be used as component(s) of liquid-crystalline media, in particular for displays based on the principle of the twisted cell, the guest-host effect, the effect of deformation of aligned phases DAP or ECB (electrically controlled birefringence), the IPS (in-plane switching) effect or the effect of dynamic scattering.

The use of certain derivatives containing a difluoromethyleneoxy bridge (—$CF_2O$—) as liquid-crystalline substances is known to the person skilled in the art. Publication JP 58035174 discloses an insecticide containing a pyridine ring and a $CF_2O$ group.

In addition, various compounds containing a difluoromethyleneoxy bridge without a pyridine ring as liquid-crystalline material and the preparation thereof have already been described, such as, for example, in publication EP 0786445 A1.

Publication U.S. Pat. No. 5,445,763 discloses smectic compounds containing a monofluorinated pyridine ring for use in ferroelectric displays. The document makes no mention of a difluoromethyleneoxy group. The compounds disclosed therein are said to achieve the object of providing nonpolar compounds of negative dielectric anisotropy, but not compounds of particularly high, positive dielectric anisotropy.

The present invention had the object of finding novel stable compounds which are suitable as component(s) of liquid-crystalline media. In particular, the compounds should simultaneously have comparatively low viscosity and a dielectric anisotropy in the positive region. For many current mixture concepts in the area of liquid crystals, it is advantageous to use compounds having high dielectric anisotropy $\Delta\epsilon$.

In view of the very wide variety of areas of application of compounds of this type having high $\Delta\epsilon$, it was desirable to have available further compounds, preferably having high nematogeneity, which have properties which are precisely customised to the particular applications.

It was thus an object of the invention to find novel stable compounds which are suitable as component(s) of liquid-crystalline media, in particular for, for example, TN, STN, IPS and TN-TFT displays.

It was a further object of the present invention to provide compounds which have, per se or in mixtures, high dielectric anisotropy $\Delta\epsilon$ and a high clearing point. In addition, the compounds according to the invention should be thermally and photochemically stable under the conditions prevailing in the areas of application. Furthermore, the compounds according to the invention should as far as possible have a broad nematic phase. As mesogens, they should facilitate a broad nematic phase in mixtures with liquid-crystalline co-components and have excellent miscibility with nematic base mixtures, in particular at low temperatures.

Surprisingly, it has been found that the pyridine derivatives according to the invention are eminently suitable as components of liquid-crystalline media. They can be used to obtain liquid-crystalline media which are particularly suitable for TN-TFT and STN displays, but also for IPS systems or more recent concepts which require particularly high dielectric anisotropies. The compounds according to the invention are particularly stable, even on exposure to air, and colourless. They are also distinguished by particularly strongly positive dielectric anisotropies $\Delta\Delta\epsilon$, due to which lower threshold voltages are required on use in optical switching elements. They have a broad nematic phase range per se or in mixtures. In addition, the compounds according to the invention have a particularly low melting point, a high clearing point and at the same time low values for the rotational viscosity $\gamma_1$. Compared with substances from the prior art, increased thermal stability, an increased clearing point and particularly high polarity (dielectric anisotropy) are observed.

The provision of the pyridine derivatives according to the invention very generally considerably broadens the range of liquid-crystalline substances which are suitable, from various applicational points of view, for the preparation of liquid-crystalline mixtures.

The invention thus relates to compounds of the formula I

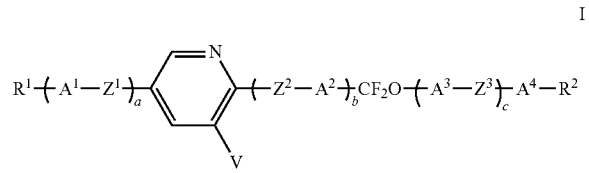

in which $R^1$ and $R^2$ each, independently of one another, denote H, F, Cl, Br, a halogenated or unsubstituted alkyl radical having 1 to 15 C atoms, in which, in addition, one or more $CH_2$ groups in these radicals may each be replaced, independently of one another, by —C≡C—, —CH=CH—, —(CO)O—, —O(CO)—, —(CO)— or —O— in such a way that O atoms are not linked directly to one another, where $R^2$ may also denote CN, SCN, NCS or $SF_5$, $A^1$, $A^2$, $A^3$ and $A^4$ each, independently of one another, identically or differently, denote:

a) trans-1,4-cyclohexylene or cyclohexenylene, in which, in addition, one or more non-adjacent $CH_2$ groups may be replaced by —O— and/or —S— and in which H may be substituted by F, b) 1,4-phenylene, in which one or two CH groups may be replaced by N and in which, in addition, one or more H atoms may be replaced by Br, Cl, F, CN, methyl, methoxy or a mono- or polyfluorinated methyl or methoxy group, or c) a radical from the group 1,4-bicyclo[2.2.2]octylene, piperidine-1,4-diyl, cyclobut-1,3-diyl, spiro[3.3]heptane-2,6-diyl,

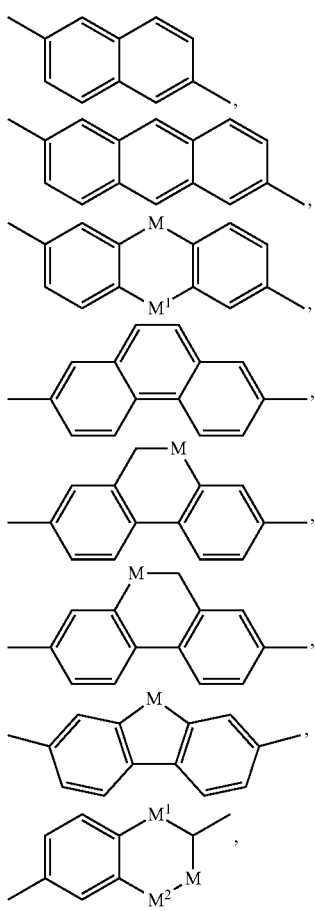

in which hydrogen atoms may be mono- or polysubstituted by F, CN, SCN, SF$_5$, CH$_2$F, CHF$_2$, CF$_3$, OCH$_2$F, OCHF$_2$ or OCF$_3$, one or more double bonds may be replaced by single bonds, M, M$^1$ or M$^2$ denotes —O—, —S—, —CH$_2$—, —CHY— or —CYY$^1$— in such a way that adjacent groups do not simultaneously denote —O— or —S—, and Y and Y$^1$ denote Cl, F, CN, OCF$_3$ or CF$_3$, V denotes H or F, Z$^1$, Z$^2$ and Z$^3$ each, independently of one another, identically or differently, denote a single bond, —CH$_2$O—, —(CO)O—, —CF$_2$O—, —CH$_2$CH$_2$CF$_2$O—, —CF$_2$CF$_2$—, —CH$_2$CF$_2$—, —CH$_2$CH$_2$—, —(CH$_2$)$_4$—, —CH═CH—, —CH═CF—, —CF═CF— or —C≡C—, where asymmetrical bridges may be oriented to both sides, and a denotes 0, 1 or 2, preferably 0 or 1,
b denotes 0, 1 or 2, preferably 1, and
c denotes 0, 1 or 2, preferably 0,
where a+b+c is ≦4, is preferably equal to 1, 2 or 3, particularly preferably 1 or 2.

A$^{1-3}$ or Z$^{1-3}$ may independently also adopt different meanings if they occur more than once for a, b or c>1.

The invention furthermore relates to the use of the compounds of the formula I in liquid-crystalline media.

The present invention likewise relates to liquid-crystalline media having at least two liquid-crystalline components which comprise at least one pyridine derivative of the formula I.

The compounds of the formula I have a broad range of applications. Depending on the choice of substituents, these compounds can serve as base materials of which liquid-crystalline media are predominantly composed; however, it is also possible to add compounds of the formula I to liquid-crystalline base materials from other classes of compounds in order, for example, to modify the dielectric and/or optical anisotropy of a dielectric of this type and/or to optimise its threshold voltage and/or its viscosity.

In the pure state, the compounds of the formula I are colourless and form, per se or in mixtures, liquid-crystalline mesophases in a temperature range which is favourably located for electro-optical use. The compounds according to the invention enable broad nematic phase ranges to be achieved. In liquid-crystalline mixtures, the compounds according to the invention increase the clearing point and increase the polarity of the mixture significantly. They can also be heated to 130° C. or more, preferably even to 150° C. or more, in air for 20 h without significant decomposition occurring.

Preference is given to compounds of the formula I in which a is 0 or 1, in particular a=1.

Z$^1$ and/or Z$^3$ preferably denote a single bond, —CF$_2$O—, —OCF$_2$—, —C$_2$F$_4$—, —CH$_2$O—, —OCH$_2$— or —(CO)O—, in particular a single bond. Z$^2$ preferably denotes —CH$_2$CH$_2$—, —CH═CH—, —C≡C— or a single bond, in particular a single bond.

In the case where Z$^2$ is a single bond, A$^2$ preferably denotes an unsaturated or aromatic ring from groups b) or c) according to the definition of formula I.

A$^1$, A$^2$, A$^3$ and A$^4$, if present, preferably denote

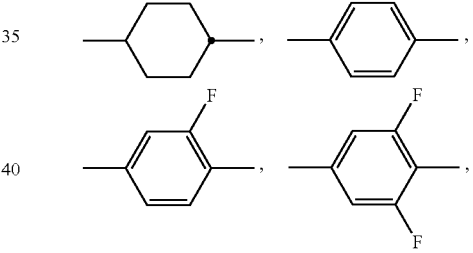

and furthermore

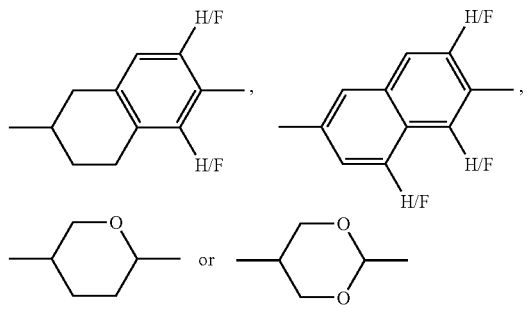

The group A$^1$ here preferably denotes

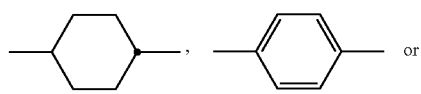

-continued

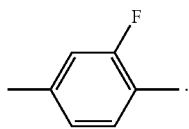

$A^2$ preferably denotes

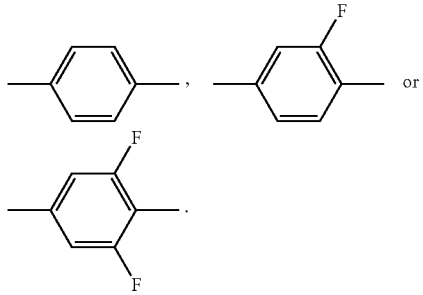

$A^4$ preferably denotes

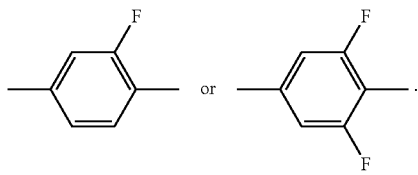

$R^1$ preferably denotes alkyl, alkoxy, alkenyl or alkenyloxy having up to 8 carbon atoms. $R^1$ particularly preferably denotes straight-chain alkyl or alkenyl.
$R^2$ preferably denotes X, where
X denotes F, Cl, $OCF_3$, $OCHF_2$, $OCHFCF_3$, $OCF_2CHFCF_3$, $CF_3$, CN, $SF_5$, NCS, in particular F, Cl, CN or $OCF_3$ and very particularly F.
$R^1$ and $R^2$ preferably do not simultaneously denote H.
Particular preference is given to compounds of the formula IA

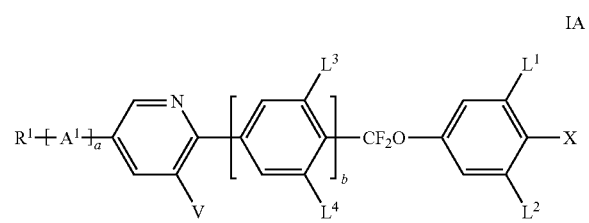

in which
$R^1$, $A^1$, X, a, b and V have the meanings indicated above for formula I, and
$L^1$, $L^2$, $L^3$ and $L^4$
denote H or F.

Preference is given to compounds of the formula IA in which $L^1$ denotes a fluorine. b preferably denotes 0 or 1, in particular 1. V is preferably H. $L^3$ is preferably F. a+b is preferably 1, 2 or 3. b is very particularly preferably 1, and a is preferably 1 or 2. 2, 3 or four of the groups $L^1$ to $L^4$ are particularly preferably a fluorine.

In a further embodiment of the invention, preference is given to compounds of the formula I in which V denotes an F and at least one of the rings $A^1$ and $A^2$ denotes a 1,4-phenylene according to group b). Particular preference is given here to compounds in which a+b is 1, 2 or 3. In particular, b is 1 and a is 1. The group $A^1$ here preferably denotes

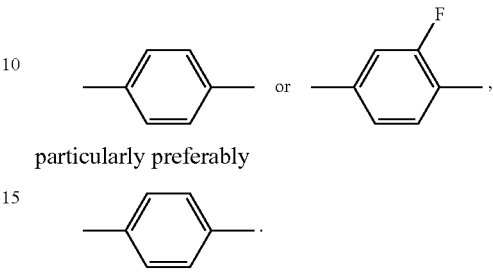

particularly preferably

Particularly preferred compounds of the formula I are the compounds of the formulae I1 to I7

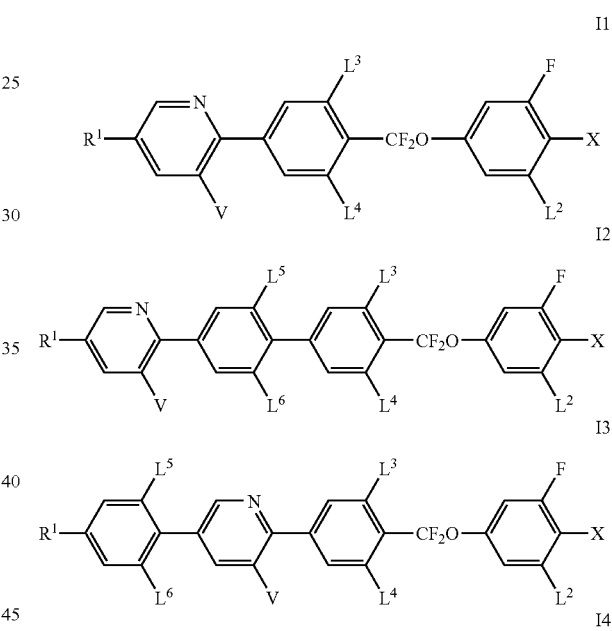

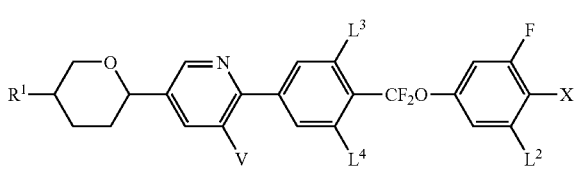

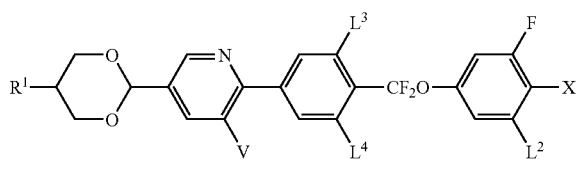

in which $R^1$, V and X have the meanings indicated above. $L^2$, $L^3$, $L^4$, $L^5$ and $L^6$, independently of one another, denote H or F.

In the case of compounds which can occur in diastereomers, both the pure substances and also every mixing ratio of the isomers are encompassed and in each case to be regarded as suitable mixture component.

The compounds of the formula I are prepared by methods known per se, as described in the literature (for example in the standard works, such as Houben-Weyl, Methoden der organischen Chemie [Methods of Organic Chemistry], Georg-Thieme-Verlag, Stuttgart), to be precise under reaction conditions which are known and suitable for the said reactions. Use can also be made here of variants known per se which are not mentioned here in greater detail.

The compounds of the formula I can advantageously be prepared as evident from the following illustrative syntheses (Schemes 1 and 2):

Scheme 1.
Variant of the synthesis of the pyridine derivatives of the formula I.

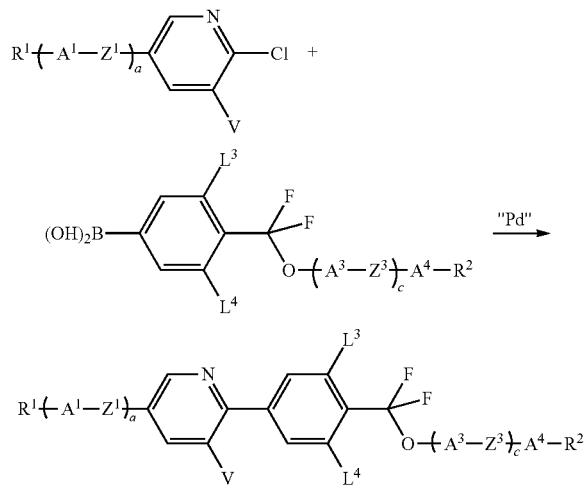

Scheme 2.
Variant of the synthesis of the pyridine derivatives of the formula I.
L = H or F.

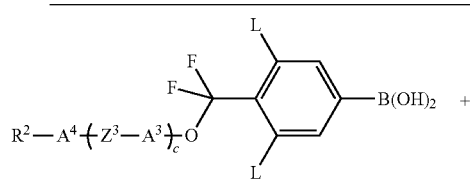

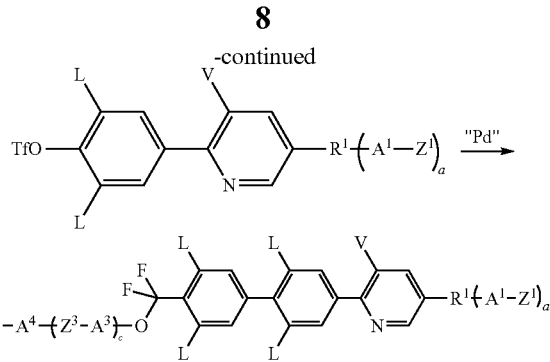

The groups of the formulae in Schemes 1 and 2 that are not involved can be varied, so long as the definitions of the compounds of the formula I suggest it. Corresponding starting materials can generally be prepared readily by the person skilled in the art. Thus, the compounds of the formula I or IA can be prepared.

The invention therefore also relates to a process for the preparation of compounds of the formula I:
A process for the preparation of compounds of the formula I in which V denotes hydrogen or fluorine is characterised in that it comprises a process step wherein a 2-substituted pyridine of the formula

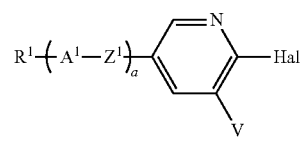  II in which $R^1$, $A^1$, $Z^1$, V and a are as defined in claim 1, and Hal denotes $OSO_2CF_3$, Cl, Br or I,
is brought to reaction with a boronic acid or an open-chain or cyclic boronic acid ester of the formulae

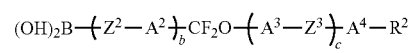  IIIa

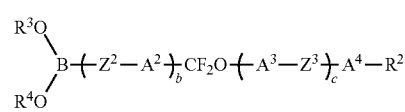  IIIb in which $Z^2$, $Z^3$, $A^2$, $A^3$, $A^4$, b, c and $R^2$ are as defined in claim 1, and
$R^3$, $R^4$ denote alkyl having 1-12 C atoms or $R^3+R^4$ together also denote a $C_1$-$C_6$-alkylene, in particular of the formulae —$CH_2$—$(CH_2)_p$—$CH_2$— and —$C(CH_3)_2C(CH_3)_2$—, or 1,2-phenylene,
where $R^3$, $R^4$ and $R^3+R^4$ may also be substituted, in particular by $C_1$-$C_6$-alkyl, F, Cl, $C_1$-$C_6$-alkoxy, and where p is 0 or 1,
in the presence of a transition-metal catalyst, preferably a palladium complex. The complexes are preferably palladium (II) complexes, in particular bis(triphenylphosphine)palladium(II) chloride. Hal preferably denotes chlorine or bromine, in particular chlorine. In IIIa/IIIb, b preferably denotes 1 or 2 and $Z^2$ denotes a single bond. Furthermore, the subforms indicated for the compounds of the formula I are preferred.

Further preferred process variants are revealed by the examples, the details of which—also generalised in accordance with general expert knowledge—are representative of preferred embodiments of the process according to the invention and products thereof.

The invention also relates to liquid-crystalline media comprising one or more of the compounds of the formula I according to the invention. The liquid-crystalline media comprise at least two components. They are preferably obtained by mixing the components with one another. A process for the preparation of a liquid-crystalline medium is therefore characterised in that at least one compound of the formula I is mixed with at least one further mesogenic compound, and additives are optionally added.

The achievable combinations of clearing point, viscosity at low temperature, thermal and UV stability and dielectric anisotropy are far superior to previous materials from the prior art.

The liquid-crystalline media according to the invention preferably comprise 2 to 40, particularly preferably 4 to 30, components as further constituents besides one or more compounds according to the invention. In particular, these media comprise 7 to 25 components besides one or more compounds according to the invention. These further constituents are preferably selected from nematic or nematogenic (monotropic or isotropic) substances, in particular substances from the classes of the azoxybenzenes, benzylideneanilines, biphenyls, terphenyls, phenyl or cyclohexyl benzoates, phenyl or cyclohexyl esters of cyclohexanecarboxylic acid, phenyl or cyclohexyl esters of cyclohexylbenzoic acid, phenyl or cyclohexyl esters of cyclohexylcyclohexanecarboxylic acid, cyclohexylphenyl esters of benzoic acid, of cyclohexanecarboxylic acid or of cyclohexylcyclohexanecarboxylic acid, phenylcyclohexanes, cyclohexylbiphenyls, phenylcyclohexylcyclohexanes, cyclohexylcyclohexanes, cyclohexylcyclohexylcyclohexanes, 1,4-biscyclohexylbenzenes, 4,4'-biscyclohexylbiphenyls, phenyl- or cyclohexylpyrimidines, phenyl- or cyclohexylpyridines, phenyl- or cyclohexyldioxanes, phenyl- or cyclohexyl-1,3-dithianes, 1,2-diphenylethanes, 1,2-dicyclohexylethanes, 1-phenyl-2-cyclohexylethanes, 1-cyclohexyl-2-(4-phenylcyclohexyl)ethanes, 1-cyclohexyl-2-biphenylethanes, 1-phenyl-2-cyclohexylphenylethanes, optionally halogenated stilbenes, benzyl phenyl ethers, tolans and substituted cinnamic acids. The 1,4-phenylene groups in these compounds may also be fluorinated. Mixtures for TFT displays preferably contain no compounds from the class of the carboxylic esters or carbonitriles.

The most important compounds suitable as further constituents of the media according to the invention can be characterised by the formulae 1, 2, 3, 4 and 5:

R'-L-E-R" 1
R'-L-COO-E-R" 2
R'-L-CF$_2$O-E-R" 3
R'-L-CH$_2$CH$_2$-E-R" 4
R'-L-C≡C-E-R" 5

In the formulae 1, 2, 3, 4 and 5, L and E, which may be identical or different, each, independently of one another, denote a divalent radical from the group formed by -Phe-, -Cyc-, -Phe-Phe-, -Phe-Cyc-, -Cyc-Cyc-, -Pyr-, -Dio-, -Py-, -G-Phe- and -G-Cyc- and mirror images thereof, where Phe denotes unsubstituted or fluorine-substituted 1,4-phenylene, Cyc denotes trans-1,4-cyclohexylene, Pyr denotes pyrimidine-2,5-diyl, Dio denotes 1,3-dioxane-2,5-diyl, Py denotes tetrahydropyran-2,5-diyl and G denotes 2-(trans-1,4-cyclohexyl)ethyl.

One of the radicals L and E is preferably Cyc, Phe or Pyr. E is preferably Cyc, Phe or Phe-Cyc. The media according to the invention preferably comprise one or more components selected from the compounds of the formulae 1, 2, 3, 4 and 5 in which L and E are selected from the group consisting of Cyc, Phe and Pyr and simultaneously one or more components selected from the compounds of the formulae 1, 2, 3, 4 and 5 in which one of the radicals L and E is selected from the group consisting of Cyc, Phe, Py and Pyr and the other radical is selected from the group consisting of -Phe-Phe-, -Phe-Cyc-, -Cyc-Cyc-, -G-Phe- and -G-Cyc-, and optionally one or more components selected from the compounds of the formulae 1, 2, 3, 4 and 5 in which the radicals L and E are selected from the group consisting of -Phe-Cyc-, -Cyc-Cyc-, -G-Phe- and -G-Cyc-.

R' and/or R" each, independently of one another, denote alkyl, alkenyl, alkoxy, alkoxyalkyl, alkenyloxy or alkanoyloxy having up to 8 C atoms, —F, —Cl, —CN, —NCS or —(O)$_i$CH$_{3-k}$F$_k$, where i is 0 or 1 and k is 1, 2 or 3.

In a smaller sub-group of the compounds of the formulae 1, 2, 3, 4 and 5, R' and R" each, independently of one another, denote alkyl, alkenyl, alkoxy, alkoxyalkyl, alkenyloxy or alkanoyloxy having up to 8 C atoms. This smaller sub-group is called group A below, and the compounds are referred to by the sub-formulae 1a, 2a, 3a, 4a and 5a. In most of these compounds, R' and R" are different from one another, one of these radicals usually being alkyl, alkenyl, alkoxy or alkoxyalkyl.

In another smaller sub-group of the compounds of the formulae 1, 2, 3, 4 and 5, which is referred to as group B, R" denotes —F, —Cl, —NCS or —(O)$_i$CH$_{3-k}$F$_k$, where i is 0 or 1 and k is 1, 2 or 3. The compounds in which R" has this meaning are referred to by the sub-formulae 1b, 2b, 3b, 4b and 5b. Particular preference is given to those compounds of the sub-formulae 1b, 2b, 3b, 4b and 5b in which R" has the meaning —F, —Cl, —NCS, —CF$_3$, —OCHF$_2$ or —OCF$_3$.

In the compounds of the sub-formulae 1b, 2b, 3b, 4b and 5b, R' has the meanings indicated in the case of the compounds of the sub-formulae 1a to 5a and is preferably alkyl, alkenyl, alkoxy or alkoxyalkyl.

In a further smaller sub-group of the compounds of the formulae 1, 2, 3, 4 and 5, R" denotes —CN. This sub-group is referred to below as group C, and the compounds of this sub-group are correspondingly described by sub-formulae 1c, 2c, 3c, 4c and 5c. In the compounds of the sub-formulae 1c, 2c, 3c, 4c and 5c, R' has the meanings indicated in the case of the compounds of the sub-formulae 1a to 5a and is preferably alkyl, alkoxy or alkenyl.

Besides the preferred compounds of groups A, B and C, other compounds of the formulae 1, 2, 3, 4 and 5 having other variants of the proposed substituents are also customary. All these substances are obtainable by methods which are known from the literature or analogously thereto.

Besides compounds of the formula I according to the invention, the media according to the invention preferably comprise one or more compounds selected from groups A, B and/or C. The proportions by weight of the compounds from these groups in the media according to the invention are preferably:

group A: 0 to 90%, preferably 20 to 90%, particularly preferably 30 to 90%;
group B: 0 to 80%, preferably 10 to 80%, particularly preferably 10 to 65%;
group C: 0 to 80%, preferably 0 to 80%, particularly preferably 0 to 50;

where the sum of the proportions by weight of the group A, B and/or C compounds present in the respective media according to the invention is preferably 5 to 90% and particularly preferably 10 to 90%.

The media according to the invention preferably comprise 1 to 40%, particularly preferably 5 to 30%, of the compounds according to the invention.

The liquid-crystal mixtures according to the invention are prepared in a manner which is conventional per se. In general, the desired amount of the components used in lesser amount is dissolved in the components making up the principal constituent, preferably at elevated temperature. It is also possible to mix solutions of the components in an organic solvent, for example in acetone, chloroform or methanol, and to remove the solvent again, for example by distillation, after thorough mixing. It is furthermore possible to prepare the mixtures in other conventional manners, for example by using premixes, for example homologue mixtures, or using so-called "multi-bottle" systems.

The dielectrics may also comprise further additives known to the person skilled in the art and described in the literature. For example, 0 to 15%, preferably 0 to 10%, of pleochroic dyes, chiral dopants, stabilisers or nanoparticles can be added. The individual compounds added are employed in concentrations of 0.01 to 6%, preferably 0.1 to 3%. However, the concentration data of the other constituents of the liquid-crystal mixtures, i.e. the liquid-crystalline or mesogenic compounds, are given here without taking into account the concentration of these additives.

The liquid-crystal mixtures according to the invention enable a significant broadening of the available parameter latitude.

The invention also relates to electro-optical displays (in particular TFT displays having two plane-parallel outer plates, which, together with a frame, form a cell, integrated non-linear elements for switching individual pixels on the outer plates, and a nematic liquid-crystal mixture having positive dielectric anisotropy and high specific resistance located in the cell) which contain media of this type, and to the use of these media for electro-optical purposes.

The expression "alkyl" encompasses straight-chain and branched alkyl groups having 1-9 carbon atoms, in particular the straight-chain groups methyl, ethyl, propyl, butyl, pentyl, hexyl and heptyl. Groups having 2-5 carbon atoms are generally preferred.

The expression "alkenyl" encompasses straight-chain and branched alkenyl groups having up to 9 carbon atoms, in particular the straight-chain groups. Particularly preferred alkenyl groups are $C_2$-$C_7$-1E-alkenyl, $C_4$-$C_7$-3E-alkenyl, $C_5$-$C_7$-4-alkenyl, $C_6$-$C_7$-5-alkenyl and $C_7$-6-alkenyl, in particular $C_2$-$C_7$-1E-alkenyl, $C_4$-$C_7$-3E-alkenyl and $C_5$-$C_7$-4-alkenyl. Examples of preferred alkenyl groups are vinyl, 1E-propenyl, 1E-butenyl, 1E-pentenyl, 1E-hexenyl, 1E-heptenyl, 3-butenyl, 3E-pentenyl, 3E-hexenyl, 3E-heptenyl, 4-pentenyl, 4Z-hexenyl, 4E-hexenyl, 4Z-heptenyl, 5-hexenyl, 6-heptenyl and the like. Groups having up to 5 carbon atoms are generally preferred.

The expression "halogenated alkyl radical" preferably encompasses mono- or polyfluorinated and/or -chlorinated radicals. Perhalogenated radicals are included. Particular preference is given to fluorinated alkyl radicals, in particular $CF_3$, $CH_2CF_3$, $CH_2CHF_2$, $CHF_2$, $CH_2F$, $CHFCF_3$ and $CF_2CHFCF_3$.

The expression "alkylene" encompasses straight-chain and branched alkanediyl groups having 1-12 carbon atoms, in particular the straight-chain groups methylene, ethylene, propylene, butylene and pentylene. Groups having 2-8 carbon atoms are generally preferred.

The total amount of compounds of the formula I in the mixtures according to the invention is not crucial. The mixtures may therefore comprise one or more further components for the purposes of optimisation of various properties. However, the observed effect on the addressing times and the threshold voltage is generally greater the higher the total concentration of compounds of the formula I.

The construction of the matrix display according to the invention from polarisers, electrode base plates and surface-treated electrodes corresponds to the usual design for displays of this type. The term usual design is broadly drawn here and also encompasses all derivatives and modifications of the matrix display, in particular also matrix display elements based on poly-Si TFTs.

A significant difference between the displays according to the invention and the hitherto conventional ones based on the twisted nematic cell consists, however, in the choice of the liquid-crystal parameters of the liquid-crystal layer.

The following examples are intended to explain the invention without restricting it. Above and below, percentage data denote percent by weight. All temperatures are indicated in degrees Celsius. Furthermore, Tg denotes glass transition temperature, C=crystalline state, N=nematic phase, Sm=smectic phase and I=isotropic phase. The data between these symbols represent the transition temperatures. Δn denotes optical anisotropy (589 nm, 20° C.), Δ∈ the dielectric anisotropy (1 kHz, 20° C.) and $γ_1$ the rotational viscosity (in the unit mPa·s).

The substituents on the saturated 1,4-substituted ring systems of the synthesis examples drawn are, unless indicated otherwise, in the trans-configuration. The other formulae stand for both configurations and preferably for the trans-configuration.

The physical, physicochemical and electro-optical parameters are determined by generally known methods, as described, inter alia, in the brochure "Merck Liquid Crystals-Licristal®-Physical Properties of Liquid Crystals-Description of the Measurement Methods", 1998, Merck KGaA, Darmstadt.

The dielectric anisotropy Δ∈ of the individual substances is determined at 20° C. and 1 kHz. To this end, 5-10% by weight of the substance to be investigated are measured dissolved in the dielectrically positive mixture ZLI-4792 (Merck KGaA), and the measurement value is extrapolated to a concentration of 100%. The optical anisotropy Δn is determined at 20° C. and a wavelength of 589.3 nm, the rotational viscosity $γ_1$ at 20° C., both likewise by linear extrapolation. The clearing point is determined on the pure substance or, if this is not possible, likewise by extrapolation from ZLI-4792.

The following abbreviations are used:

| | |
|---|---|
| p-TsOH | p-toluenesulfonic acid |
| THF | tetrahydrofuran |
| MTB ether | methyl t-butyl ether |
| RT | room temperature |
| BuLi | n-butyllithium |
| DMAP | N,N-dimethylaminopyridine |
| DCC | dicyclohexylcarbodiimide |
| OBN | benzyloxy substituent |
| TLC | thin layer chromatography |
| DAST | diethylaminosulfur trifluoride |
| Pd/C | palladium catalyst on support (carbon, about 5% of Pd) |

EXAMPLE 1

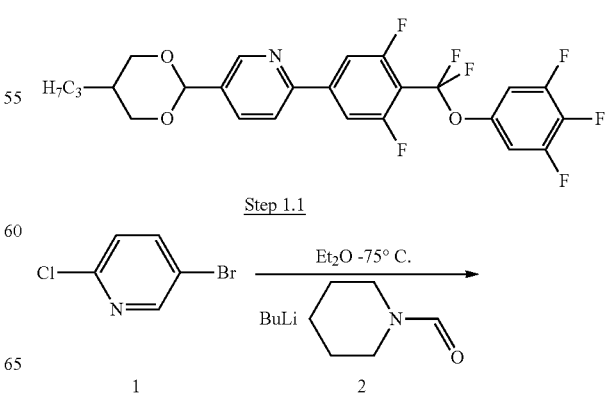

-continued

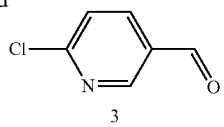

85 ml of 15% BuLi in n-hexane are added under nitrogen at −70° C. to a solution of the pyridine 1 (25.0 g; 120 mmol) in 300 ml of diethyl ether. After 90 min, a solution of 13.7 ml (120 mmol) of formylpiperidine (2) is added to the batch, likewise at low temperature. After a further hour, the batch is warmed to −10° C., water is added, and the mixture is diluted with MTB ether. The organic phase is dried over sodium sulfate and evaporated. The residue obtained is passed through silica gel (MTB ether/n-heptane 1:1). The product is subsequently crystallised from n-heptane at −20° C.

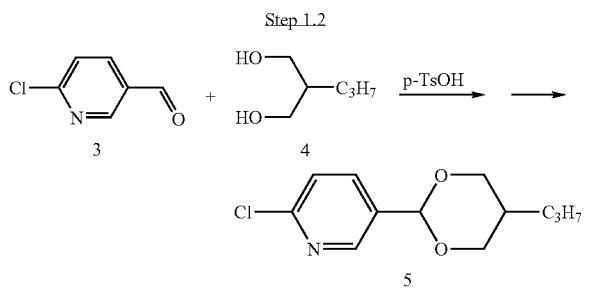

100 ml of toluene are added to 13.1 g (111 mmol) of the diol 4, 17.5 g (90%; 111 mmol) of the aldehyde 3 and 1 g of p-toluenesulfonic acid, and the mixture is heated on a water separator for 3 h. The cooled batch is passed through silica gel (toluene). The product obtained is employed in the subsequent step without further purification.

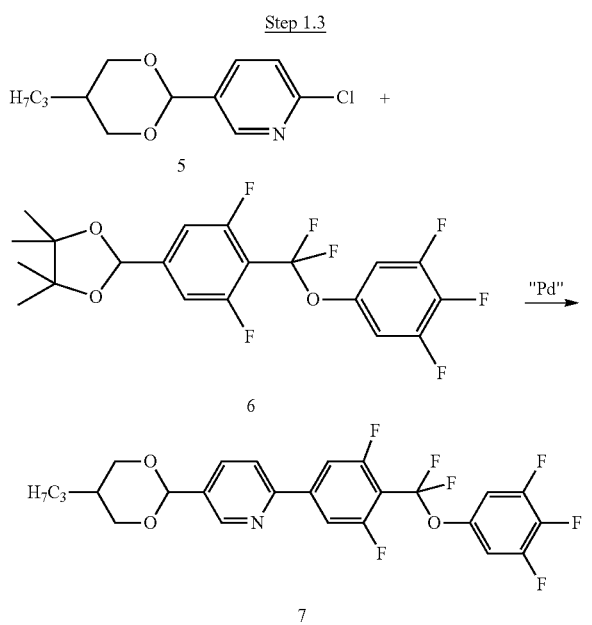

11.1 g (40 mmol) of sodium metaborate octahydrate are initially introduced in 32 ml of water, and 40 ml of THF, 0.1 ml (0.7 mmol) of hydrazinium hydroxide and 0.6 g (0.8 mmol) of bis(triphenylphosphine)palladium(II) chloride are added, and the mixture is stirred at RT for 5 min. A solution of 17.4 g (40 mmol) of the boronic acid ester 6 and 9.7 g (40 mmol) of the chloride 5 is subsequently added to the batch. After 16 h under reflux, the reaction mixture is diluted with MTB ether. The organic phase is evaporated. The residue is filtered through silica gel (toluene). The final purification of the product is carried out by crystallisation from EtOH/MTB ether.

C 125 SmA (107) N 137 I
Δε 39
Δn 0.141

The following are prepared analogously:

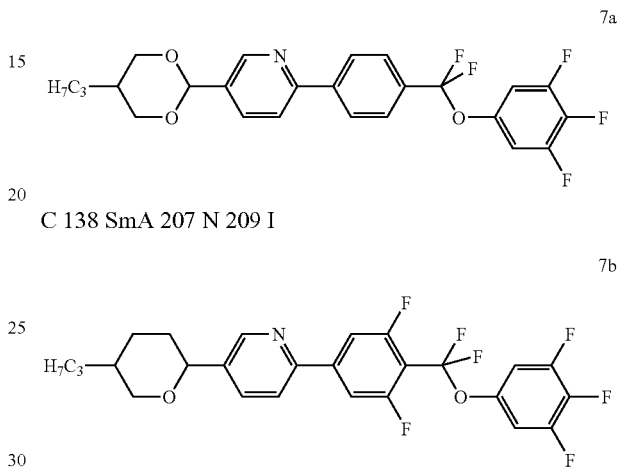

C 138 SmA 207 N 209 I

C 57 SmA 58 N 126 I
Δε 33
Δn 0.160

EXAMPLE 2

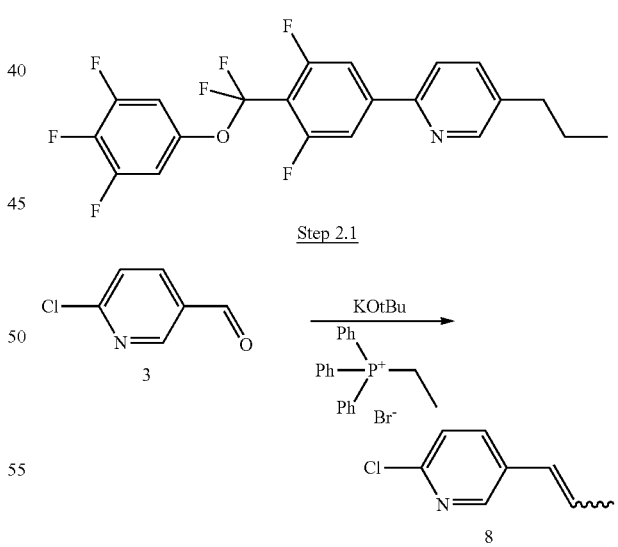

33.6 g (90 mmol) of the Wittig salt and 14.8 g (86%; 90 mmol) of the aldehyde 3 are suspended in 140 ml of THF, and 10.1 g (90 mmol) of potassium tert-butoxide are added in portions at a temperature below 20° C. The batch is stirred overnight at RT. After the addition of water, the batch is extracted with n-heptane. The organic phase is evaporated and filtered through silica gel with n-heptane/MTB ether (7:3), giving a yellow liquid 8.

Step 2.2

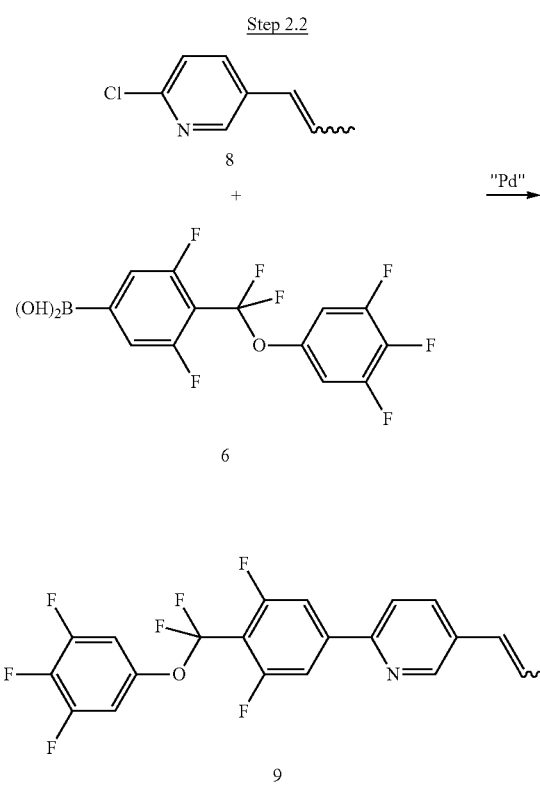

11.1 g (40 mmol) of sodium metaborate octahydrate are initially introduced in 32 ml of water, and 32 ml of THF, 0.1 ml (0.7 mmol) of hydrazinium hydroxide and 0.6 g (0.8 mmol) of bis(triphenylphosphine)palladium(II) chloride are added, and the mixture is stirred at RT for 5 min. A solution of 40.9 g (35%; 40 mmol) of the boronic acid 6 and 6.7 g (43.8 mmol) of the chloride 8 is subsequently added to the batch. After 16 h under reflux, the reaction mixture is diluted with MTB ether. The organic phase is evaporated. The residue is filtered through silica gel (n-heptane). The final purification of the product is carried out by crystallisation from heptane.

7.0 g (90%, 12 mmol) of the alkene 9 are dissolved in THF and hydrogenated on a palladium catalyst (5% of Pd on carbon). The solution is subsequently evaporated, and the residue is passed through silica gel (toluene/n-heptane 1:1). The further purification is carried out by crystallisation from n-heptane.

C 37 I

Δε 31

Δn 0.127

γ₁ 65 mPa·s

The following are prepared analogously:

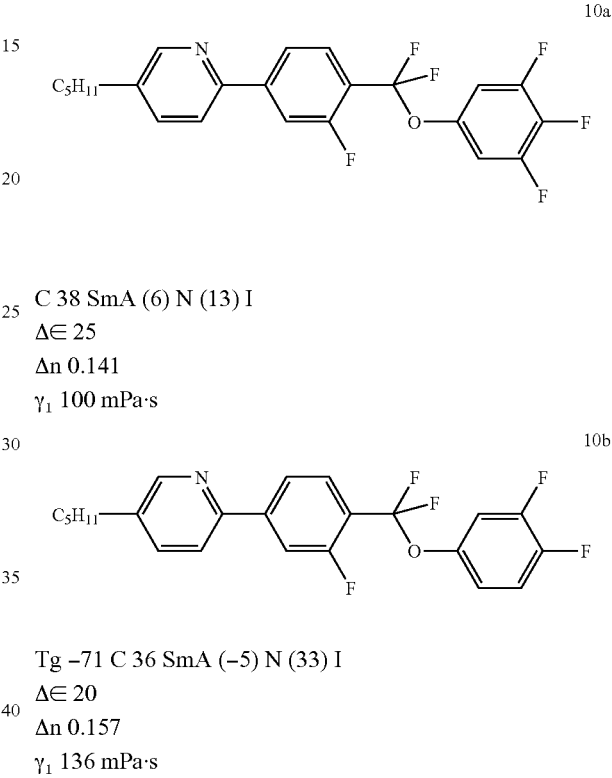

C 38 SmA (6) N (13) I

Δε 25

Δn 0.141

γ₁ 100 mPa·s

Tg −71 C 36 SmA (−5) N (33) I

Δε 20

Δn 0.157

γ₁ 136 mPa·s

Step 2.3

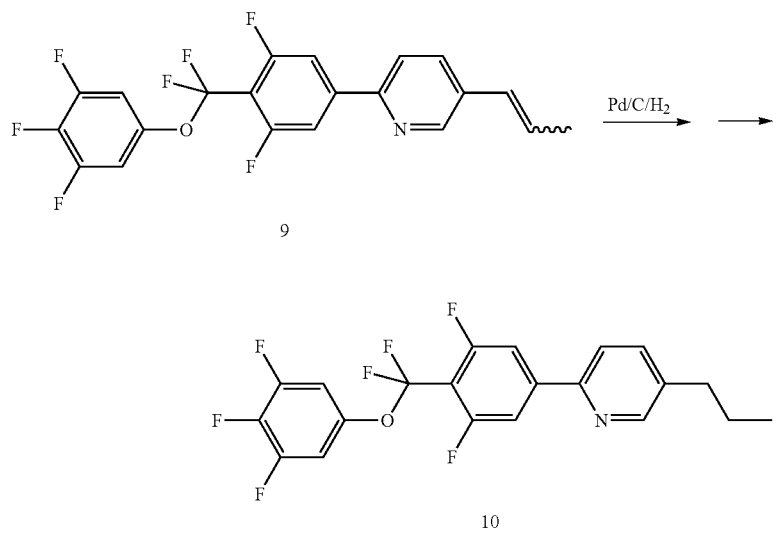

10c

C 40 SmA (–4) N (0) I
Δε 27
Δn 0.144
γ₁ 97 mPa·s

EXAMPLE 3

10d

Compound 10d is prepared analogously to Example 2, step 2.2, from the boronic acid 6 and 2-chloro-5-methylpyridine.
C 78 I
Δε 35
Δn 0.137
γ₁ 69 mPa·s The following compound 10e is likewise prepared analogously:

10e

C 122 I
Δε 27
Δn 0.182
γ₁ 76 mPa·s

EXAMPLE 4

Step 4.1

180 ml (290 mmol) of 15% BuLi in n-hexane are added under nitrogen at –70° C. to a solution of the pyridine 1 (50.0 g; 260 mmol) in 400 ml of diethyl ether. After 60 min, a solution of 36.4 g (260 mmol) of the ketone 11 in 200 ml of diethyl ether is added to the batch, likewise at low temperature. After a further hour, the batch is warmed to –20° C. and added to ice-water. The organic phase is dried over sodium sulfate and evaporated. The residue obtained is employed in the subsequent step without further purification.

Step 4.2

Under nitrogen, 66 g (260.0 mmol) of the alcohol 12 are dissolved in 800 ml of dichloromethane and 108 ml of triethylamine, and 26.2 ml (340 mmol) of methanesulfonyl chloride (MsCl) are added at 0° C. The batch is stirred overnight at RT. The reaction mixture is subsequently added to water and extracted with MTB ether. The organic phase is evaporated, and the residue obtained is passed through silica gel (MTB ether/n-heptane 1:4). The residue is employed in the following step without further purification.

Step 4.3

8.7 g (30 mmol) of sodium metaborate octahydrate are initially introduced in 15 ml of water, and 40 ml of THF, 0.10 ml of hydrazinium hydroxide and 300 mg of bis(triphenylphosphine)palladium(II) chloride are added, and the mixture is stirred at RT for 5 min. A solution of 21.5 g (35%; 20 mmol) of the boronic acid 6 and 4.7 g (20 mmol) of the chloride 13 is subsequently added to the batch. After 15 h under reflux, the reaction mixture is extracted with MTB ether. The organic phase is evaporated. The residue is filtered through silica gel (n-heptane). The final purification of the product is carried out by crystallisation from heptane.

C 73 SmA (73) N 138 I
Δε 30
Δn 0.197

The following are prepared analogously:

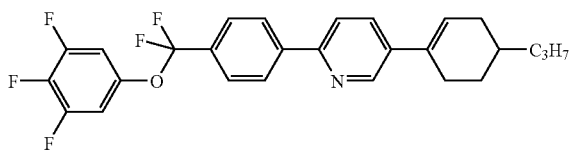
14a

C 100 SmC 107 SmA 184 N 195 I
Δε 24
Δn 0.215

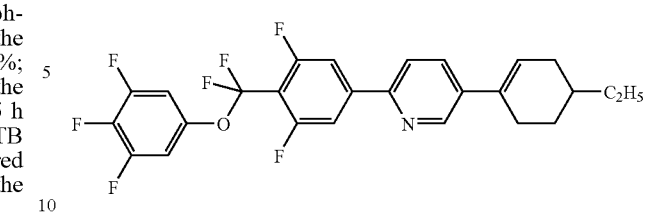
14b

C 74 SmA (50) N 111 I
Δε 32
Δn 0.191

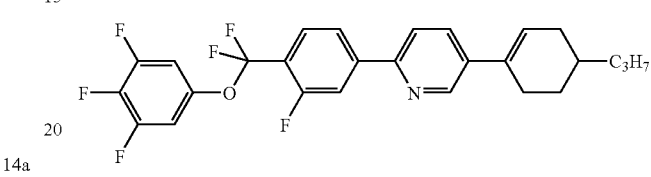
14c

C 54 SmC 55 SmA 136 N 168 I
Δε 26
Δn 0.211

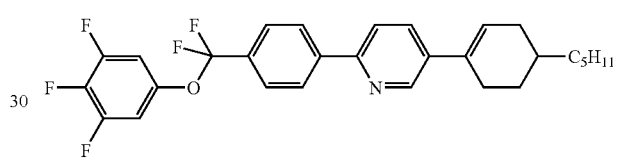
14d

C 87 SmC 103 SmA 179 N 192 I
Δε 23
Δn 0.213

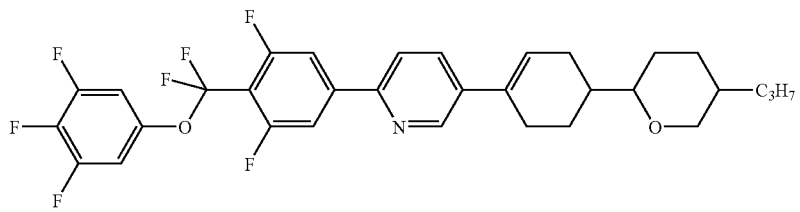
14e

C 81 SmC 125 N 257 I
Δε 33
Δn 0.209

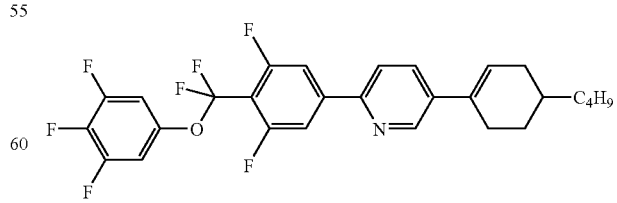
14f

C 62 SmA 82 N 133 I
Δε 29
Δn 0.194
$\gamma_1$ 402 mPa·s

EXAMPLE 5

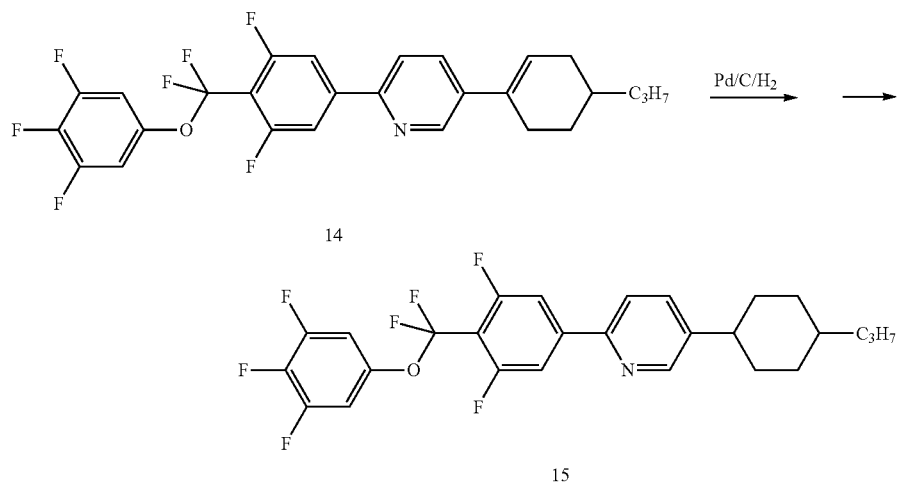

7.0 g (90%, 12 mmol) of the alkene 14 (cf. Example 4) are dissolved in THF and hydrogenated on a palladium catalyst. The solution is subsequently evaporated, and the residue is passed through silica gel (toluene/n-heptane 1:1). The further purification is carried out by crystallisation from n-heptane.

C 73 N 137 I
Δε 28
Δn 0.156

The following are prepared analogously:

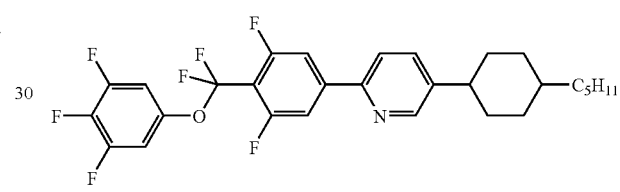

C 99 SmA 177 N 174 I
Δε 22
Δn 0.170

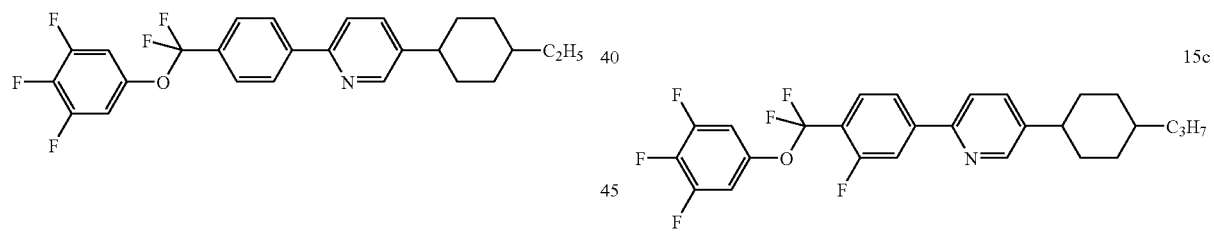

C 51 N 137 I
Δε 28
Δn 0.159

C 73 N 172 I
Δε 24
Δn 0.171

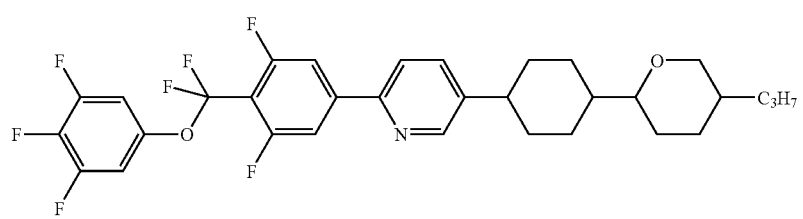

C 93 N 260 I
Δε 31
Δn 0.169

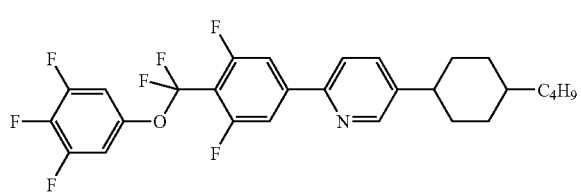

C 52 N 133 I
Δε 27
Δn 0.149

EXAMPLE 6

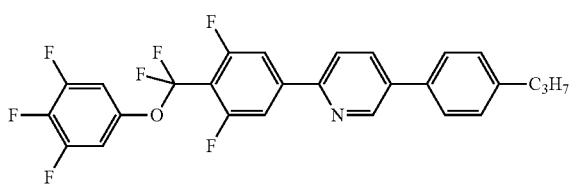

Step 6.1

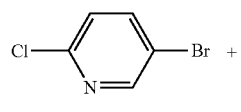

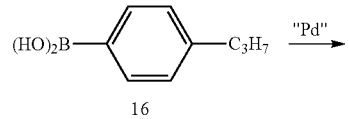

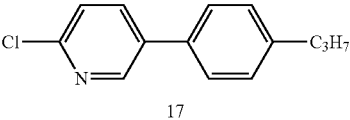

0.7 g of tetrakis(triphenylphosphine)palladium, 8.2 g (50 mmol) of the boronic acid 16 and 9.6 g (50 mmol) of the pyridine 1 are added to a mixture of 100 ml of toluene and 50 ml of 2 N sodium carbonate solution. After 60 h at 60° C., the reaction mixture is diluted with MTB ether. The organic phase is evaporated. The residue is filtered through silica gel (n-heptane).

Step 6.2

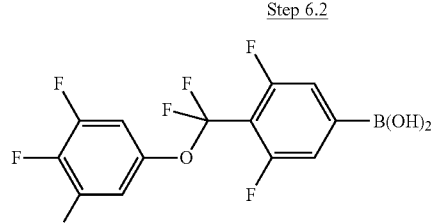

+

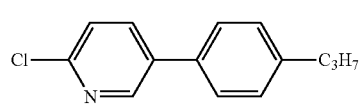

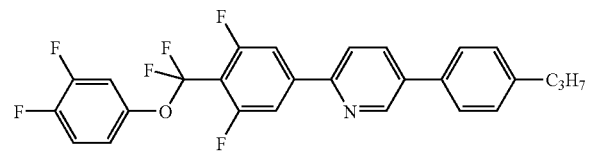

12.6 g (45 mmol) of sodium metaborate octahydrate are initially introduced in 23 ml of water, and 25 ml of THF, 0.1 ml (0.7 mmol) of hydrazinium hydroxide and 0.7 g (1 mmol) of bis(triphenylphosphine)palladium(II) chloride are added, and the mixture is stirred at RT for 5 min. A solution of 10.5 g (30 mmol) of the boronic acid 6 and 7.0 g (30 mmol) of the chloride 17 is subsequently added to the batch. After 16 h under reflux, the reaction mixture is diluted with MTB ether. The organic phase is evaporated. The residue is filtered through silica gel (n-heptane). The final purification of the product is carried out by crystallisation from heptane.

C 81 SmA 106 N 143 I
Δε 33
Δn 0.236

The following are prepared analogously:

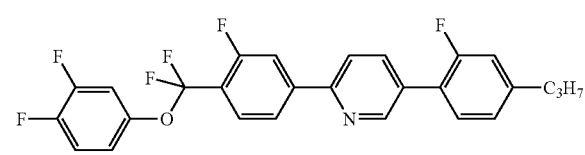

C 83 SmA 128 N 168 I
Δε 26
Δn 0.250

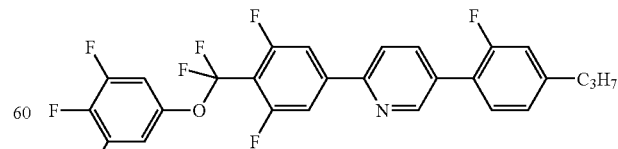

C 50 SmA 130 N 177 I
Δε 25
Δn 0.241

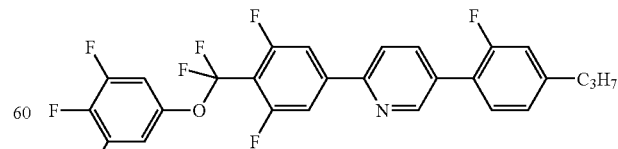

C 85 SmA (82) N 123 I
Δε 36
Δn 0.213

EXAMPLE 7

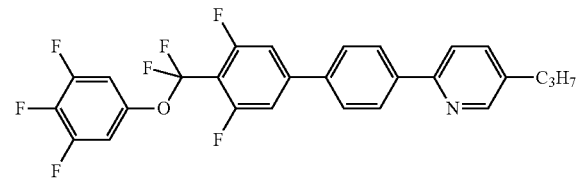

Step 7.1

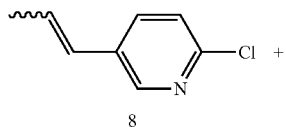

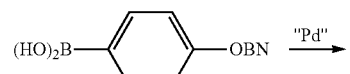

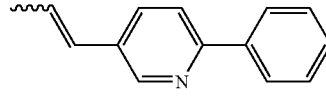

21 g (75 mmol) of sodium metaborate octahydrate are initially introduced in 38 ml of water, and 40 ml of THF, 0.15 ml (1 mmol) of hydrazinium hydroxide and 0.7 g (1 mmol) of bis(triphenylphosphine)palladium(II) chloride are added, and the mixture is stirred at RT for 5 min. A solution of 11.4 g (50 mmol) of the 4-benzyloxyphenylboronic acid 19 and 7.7 g (50 mmol) of the chloride 8 is subsequently added to the batch. After 6 h under reflux, the reaction mixture is diluted with MTB ether. The organic phase is evaporated. The residue is filtered through silica gel (n-heptane).

Step 7.2

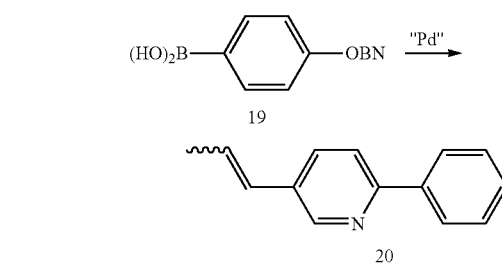

7.5 g (25 mmol) of the alkene 20 are dissolved in THF and hydrogenated on a palladium catalyst. The solution is subsequently evaporated, and the residue is passed through silica gel (toluene/MTB ether 1:1).

Step 7.3

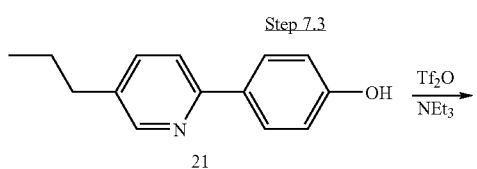

7.5 g (25 mmol) of the phenol 21 are dissolved in 700 ml of dichloromethane, and 55 ml of triethylamine and 700 mg of dimethylaminopyridine are added. 41 ml (25 mmol) of trifluoromethanesulfonic anhydride (Tf$_2$O) are subsequently added dropwise over the course of 30 min at 5° C. After 17 h at RT, the batch is diluted with n-heptane and passed through silica gel (MTB ether/heptane 1:2). The product is employed in the subsequent step without further purification.

Step 7.4

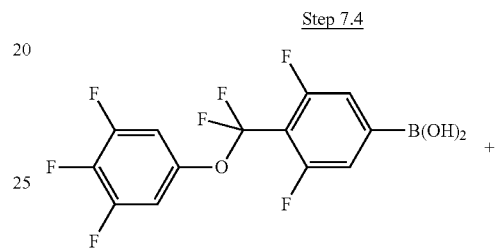

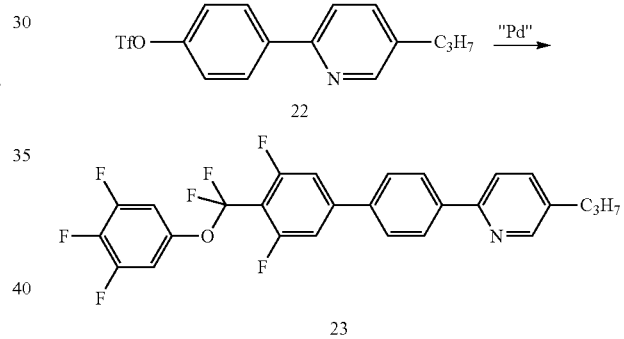

8.4 g (30 mmol) of sodium metaborate octahydrate are initially introduced in 15 ml of water, and 15 ml of THF, 0.15 ml (1 mmol) of hydrazinium hydroxide and 0.7 g (1 mmol) of bis(triphenylphosphine)palladium(II) chloride are added, and the mixture is stirred at RT for 5 min. A solution of 7.0 g (20 mmol) of the boronic acid 6 and 6.9 g (20 mmol) of the triflate 22 is subsequently added to the batch. After 16 h under reflux, the reaction mixture is diluted with MTB ether. The organic phase is evaporated. The residue is filtered through silica gel (n-heptane/toluene). The final purification of the product 23 is carried out by crystallisation from heptane.

EXAMPLE 8

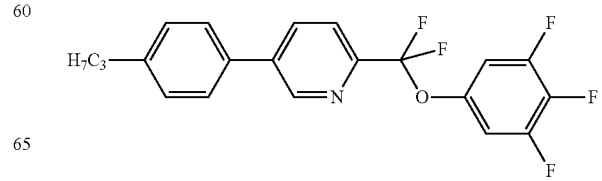

Step 8.1

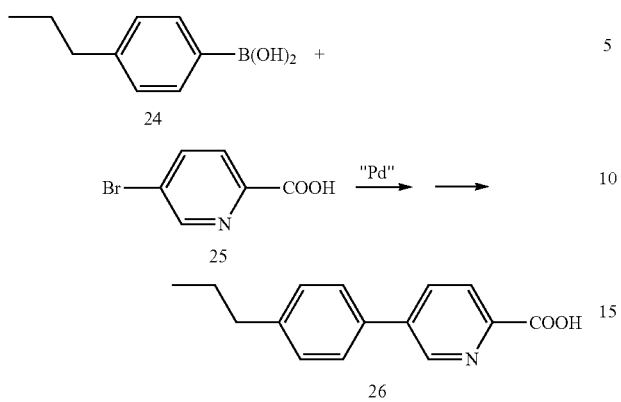

8.4 g (30 mmol) of sodium metaborate octahydrate are initially introduced in 15 ml of water, and 15 ml of THF, 0.15 ml (1 mmol) of hydrazinium hydroxide and 0.7 g (1 mmol) of bis(triphenylphosphine)palladium(II) chloride are added, and the mixture is stirred at RT for 5 min. A solution of 3.3 g (20 mmol) of the boronic acid 24 and 4.1 g (20 mmol) of the bromide 25 is subsequently added to the batch. After 16 h under reflux, the reaction mixture is diluted with MTB ether and adjusted to pH 6. The organic phase is evaporated. The residue is employed in the subsequent step without further purification.

Step 8.2

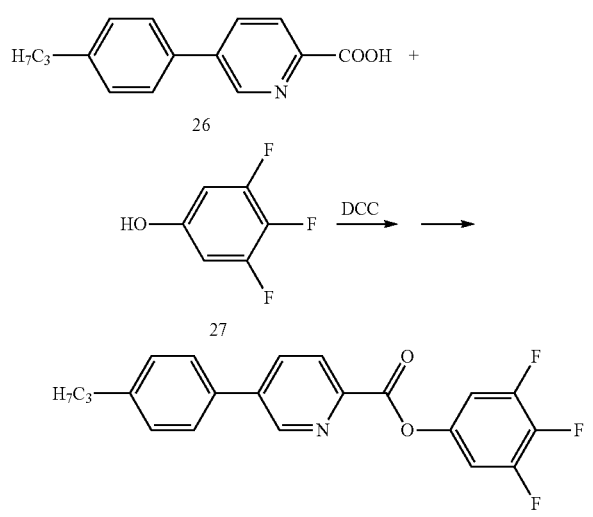

12.1 g (50 mmol) of the acid 26, 7.4 g (50 mmol) of the phenol 27 and 270 mg of DMAP are initially introduced in 70 ml of toluene under nitrogen and cooled to 0° C., and a solution of 11.3 g (55 mmol) of DCC in 300 ml of toluene is added at a max. of 5° C. The batch is stirred overnight at RT. 6.1 g of oxalic acid are subsequently added to the mixture, which is then stirred again at RT for 1 h. The reaction mixture is cooled to 0 to 5° C., and the precipitated solid is separated off. The filtrate is evaporated to dryness in a rotary evaporator. The residue is passed through silica gel (MTB ether/heptane 1:1).

Step 8.3

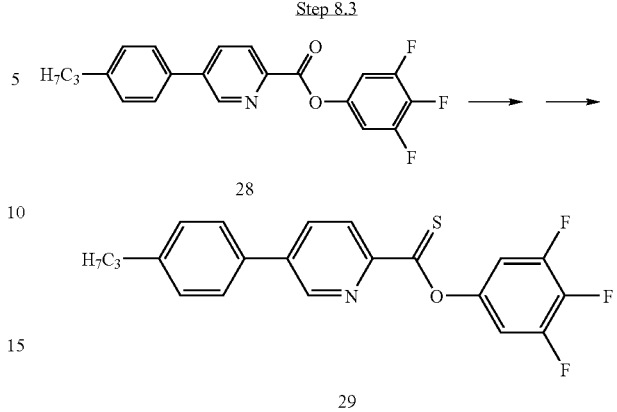

500 ml of chlorobenzene are added to 37.1 g (100 mmol) of the ester 28 and 50.6 g (130 mmol) of Lawesson's reagent (2,4-bis(4-methoxyphenyl)-1,3,2,4-dithiadiphosphetane 2,4-disulfide), and the mixture is heated at the boil to complete conversion of the ester 28 (TLC monitoring). The cooled batch is filtered through silica with suction, and the filtrate is evaporated. The residue is purified on silica gel.

Step 8.4

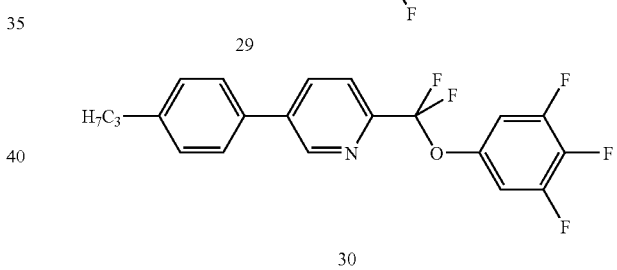

7.7 g (20 mmol) of the thioester 29 are dissolved in 40 ml of dichloromethane, and 26.7 ml (20 mmol) of DAST are added at 20°, and the mixture is stirred at 60° for 48 h. The cooled batch is poured into saturated NaHCO$_3$ solution and extracted with dichloromethane. The organic phase is dried over sodium sulfate and evaporated in a rotary evaporator. The residue is purified on silica gel (MTB ether/heptane 1:2).

EXAMPLES 9 a-f)

Using the starting material of the formula (31)

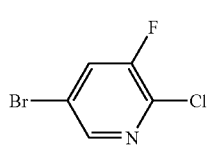

instead of the pyridine 1, the following compounds are obtained analogously to Examples 1, 3, 4, 5, 6 and 7:

9.a) ANALOGOUSLY TO EXAMPLE 1

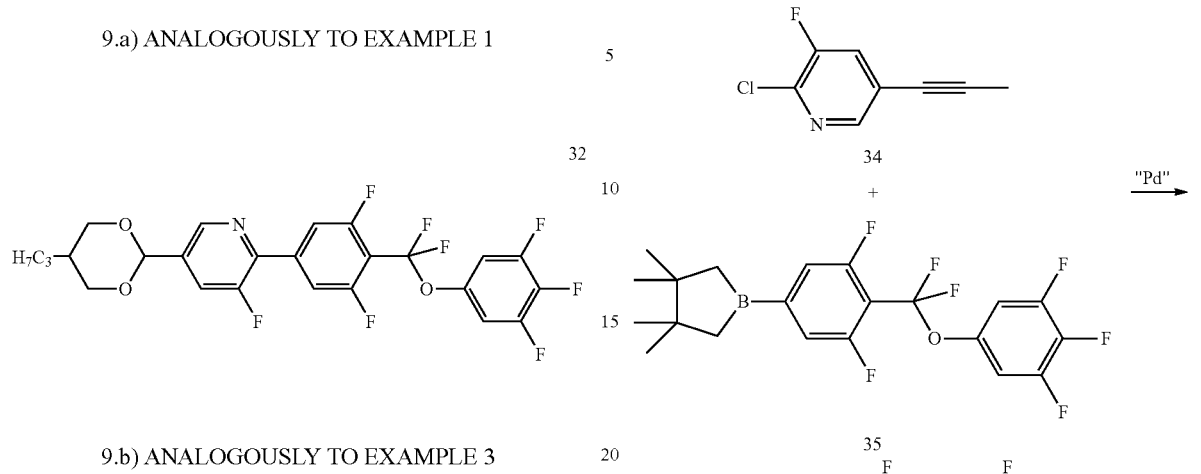

9.b) ANALOGOUSLY TO EXAMPLE 3

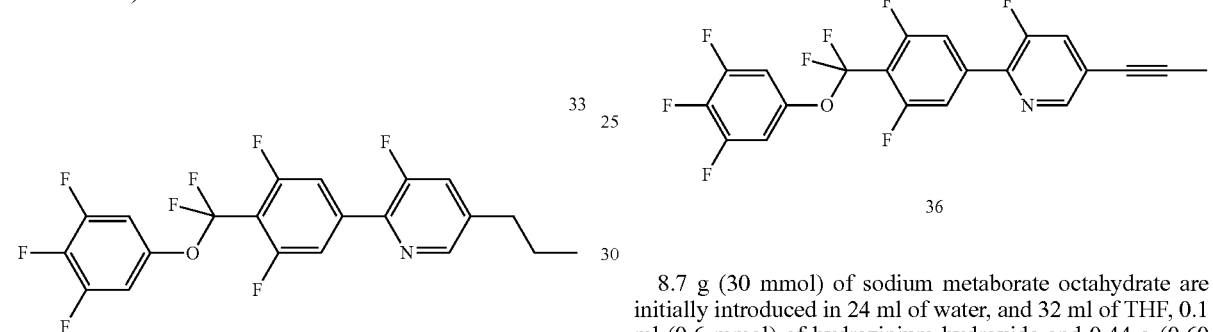

Step 9b.1

21.1 g (100 mmol) of 5-bromo-2-chloro-3-fluoropyridine 31 are dissolved in 300 ml of THF and 340 ml of triethylamine. 6.1 g (150 mmol) of propyne are passed into this solution at 0° C. 2.8 g (4 mmol) of bis(triphenylphosphine)palladium(II) chloride and 380 mg (2.0 mmol) of Cu(I) iodide are subsequently added, and the mixture is stirred at RT for 12 h. The crude product 34 is evaporated and filtered through silica gel with n-heptane/MTB ether (8:2), giving a dark oil, which is employed in the next step.

Step 9b.2

8.7 g (30 mmol) of sodium metaborate octahydrate are initially introduced in 24 ml of water, and 32 ml of THF, 0.1 ml (0.6 mmol) of hydrazinium hydroxide and 0.44 g (0.60 mmol) of bis(triphenylphosphine)palladium(II) chloride are added, and the mixture is stirred at RT for 5 min. A solution of 13.1 g (30 mmol) of the boronic acid ester 35 and 7.27 g (30 mmol) of the chloropyridine 34, dissolved in 32 ml of THF, is subsequently added to the batch. After 8 h under reflux, the reaction mixture is diluted with MTB ether. The organic phase is evaporated. The residue is filtered through 100 ml of silica gel (n-heptane/MTB ether). The final purification of compound 36 is carried out by crystallisation from heptane.

C 90 N (72) I

Δε 42

Δn 0.211

Step 9b.3

The alkyne 36 is hydrogenated on the end group analogously to step 2.3 to give the desired product 33.

C 32 I

Δε 37

Δn 0.126

9.c) ANALOGOUSLY TO EXAMPLE 4

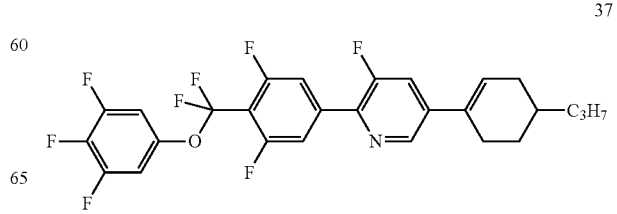

-continued

Step 9c.1

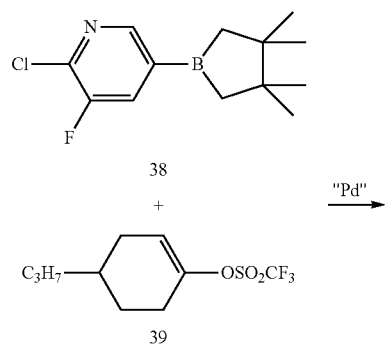

Analogously to step 9b.2, 16.6 g (63.1 mmol) of the boronic acid ester 38 (from 31 by Pd coupling to bispinacolatodiboron) are reacted with 21.8 g (80 mmol) of the cyclohexene triflate 39 with palladium catalysis to give compound 40 and worked up.

Step 9c.2

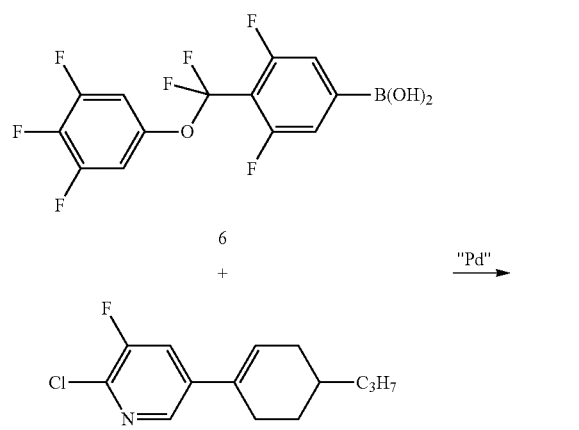

The reaction of 40 with 6 to give the desired product 37 is carried out analogously to step 4.3.

9.d) ANALOGOUSLY TO EXAMPLE 5

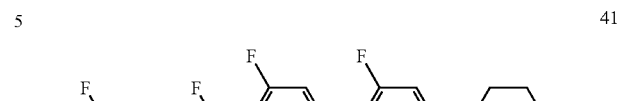

Compound 37 is hydrogenated analogously to Example 5 to give compound 41.

9.e) ANALOGOUSLY TO EXAMPLE 6

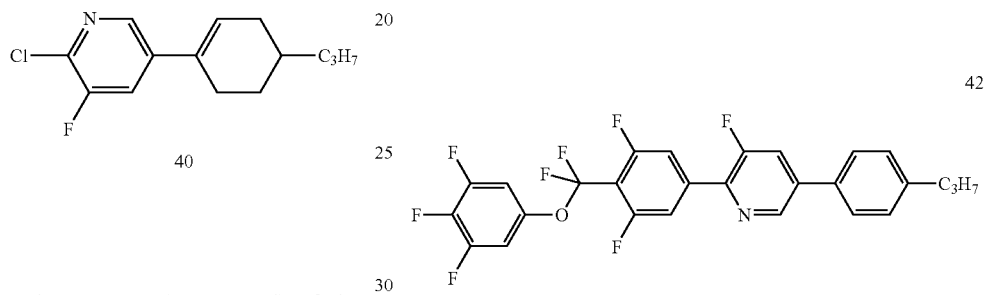

Tg −51 C 60 SmA 85 N 128 I

Δε 38

Δn 0.226

γ$_1$ 250 mPa·s

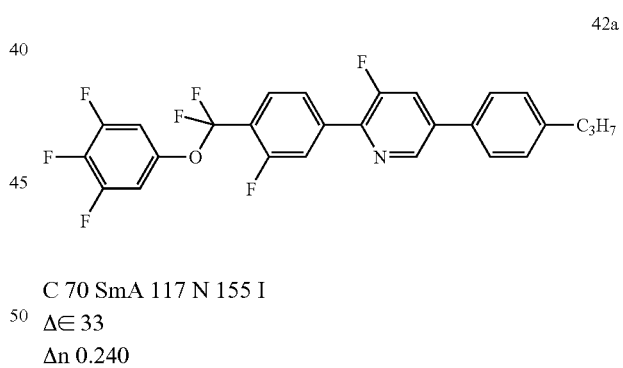

C 70 SmA 117 N 155 I

Δε 33

Δn 0.240

9.f) ANALOGOUSLY TO EXAMPLE 7

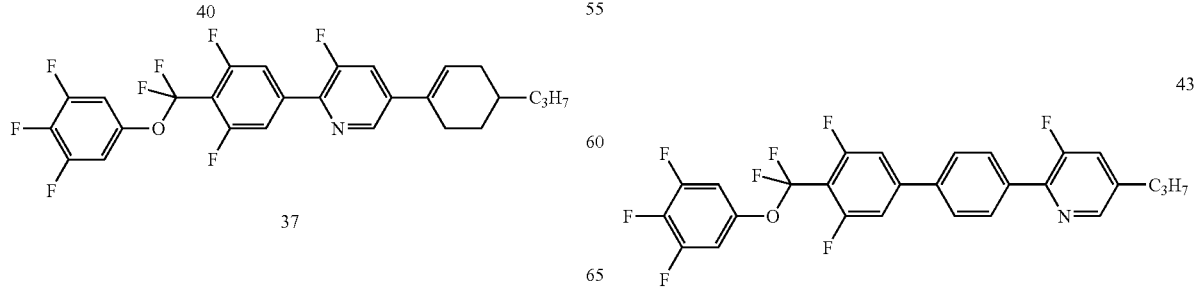

Further combinations of the embodiments and variants of the invention in accordance with the description also arise from the following claims.

The invention claimed is:
1. A compound of formula I

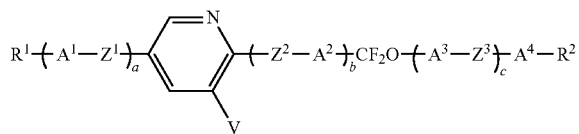

in which
$R^1$ and $R^2$ each, independently of one another, denote H, F, Cl, Br, a halogenated or unsubstituted alkyl radical having 1 to 15 C atoms, in which, in addition, one or more $CH_2$ groups in these radicals may each be replaced, independently of one another, by —C≡C—, —CH═CH—, —(CO)O—, —O(CO)—, —(CO)— or —O— in such a way that O atoms are not linked directly to one another, where $R^2$ may also denote CN, SCN, NCS or $SF_5$, $A^1$, $A^2$, $A^3$ and $A^4$ each, independently of one another, identically or differently, denote:
  a) trans-1,4-cyclohexylene or cyclohexenylene, in which, in addition, one or more non-adjacent $CH_2$ groups may be replaced by —O— and/or —S— and in which H may be substituted by F,
  b) 1,4-phenylene, in which one or two CH groups may be replaced by N and in which, in addition, one or more H atoms may be replaced by Br, Cl, F, CN, methyl, methoxy or a mono- or polyfluorinated methyl or methoxy group, or
  c) a radical from the group 1,4-bicyclo[2.2.2]octylene, piperidine-1,4-diyl, cyclobut-1,3-diyl, spiro[3.3]heptane-2,6-diyl,

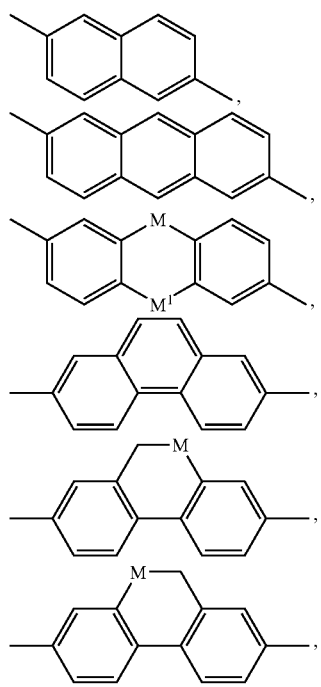

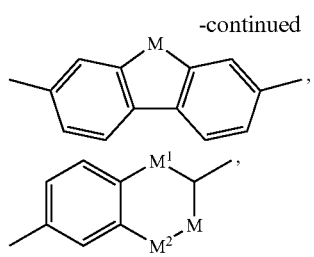

in which hydrogen atoms may be mono- or polysubstituted by F, CN, SCN, $SF_5$, $CH_2F$, $CHF_2$, $CF_3$, $OCH_2F$, $OCHF_2$ or $OCF_3$, one or more double bonds may be replaced by single bonds, M, $M^1$ or $M^2$ denotes —O—, —S—, —$CH_2$—, —CHY— or —$CYY^1$— in such a way that adjacent groups do not simultaneously denote —O— or —S—, and Y and $Y^1$ denote Cl, F, CN, $OCF_3$ or $CF_3$, V denotes H or F,
$Z^1$, $Z^2$ and $Z^3$
  each, independently of one another, identically or differently, denote a single bond, —$CH_2O$—, —(CO)O—, —$CF_2O$—, —$CH_2CH_2CF_2O$—, —$CF_2CF_2$—, —$CH_2CF_2$—, —$CH_2CH_2$—, —$(CH_2)_4$—, —CH═CH—, —CH═CF—, —CF═CF— or —C≡C—, where asymmetrical bridges may be oriented to both sides, and
a denotes 0, 1 or 2,
b denotes 0, 1 or 2, and
c denotes 0, 1 or 2,
where a+b+c is ≦4.

2. The compound according to claim 1 of formula IA

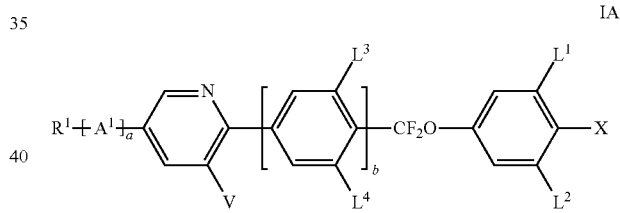

in which
$R^1$, $A^1$, a, b and V have the meanings indicated for formula I in claim 1,
X denotes F, $OCF_3$, CN, $CF_3$, SCN, $SF_5$, NCS, Cl, $OCHF_2$, $OCHFCF_3$, $OCF_2CHFCF_3$,
V denotes H or F, and
$L^1$, $L^2$, $L^3$ and $L^4$ each, independently of one another, denote H or F.

3. The compound according to claim 1, wherein $R^1$ denotes alkyl, alkoxy, alkenyl or alkenyloxy having up to 8 carbon atoms.

4. The compound according to claim 1, wherein $L^1$ denotes fluorine and $L^2$ independently denotes fluorine or hydrogen.

5. The compound according to claim 1 of formulae I1 to I7

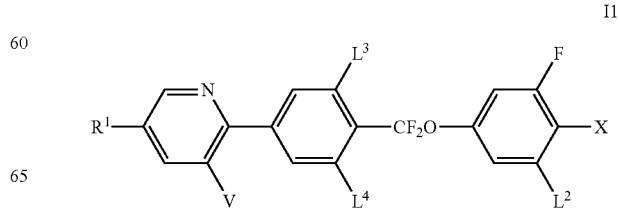

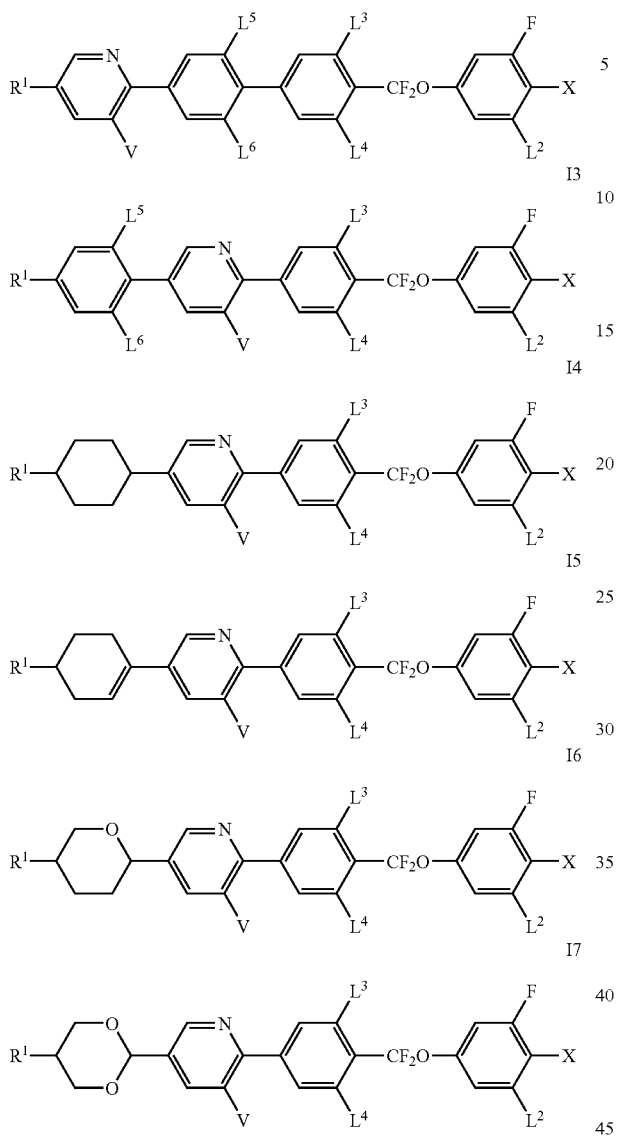

in which $R^1$ and V have the meanings indicated in claim 1, and

X denotes F, $OCF_3$, CN, $CF_3$, SCN, $SF_5$, NCS, Cl, $OCHF_2$, $OCHFCF_3$, $OCF_2CHFCF_3$, and $L^2$, $L^3$, $L^4$, $L^5$ and $L^6$ denote H or F.

6. The compound according to claim 1, wherein $L^1$ and $L^2$ denote fluorine.

7. The compound according to claim 1, wherein V denotes hydrogen.

8. The compound according to claim 1, wherein V denotes fluorine.

9. A process for the preparation of a compound of formula I according to claim 1 in which V denotes fluorine or hydrogen, comprising a process step wherein a 2-substituted pyridine of the formula

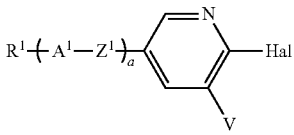

in which $R^1$, $A^1$, $Z^1$ and a are as defined in claim 1, and

Hal denotes $OSO_2CF_3$, Cl, Br or I, is reacted with a boronic acid or an open-chain or cyclic boronic acid ester of the formulae

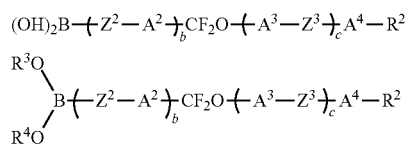

in which $Z^2$, $Z^3$, $A^2$, $A^3$, $A^4$, a, b and $R^2$ are as defined in claim 1, and $R^3$, $R^4$ denote alkyl having 1-12 C atoms or $R^3+R^4$ together also denote a $C_2$-$C_8$-alkylene or a 1,2-phenylene, where $R^3$, $R^4$ and $R^3+R^4$ may also be substituted, in the presence of a transition-metal catalyst.

10. A method of using one or more compounds of the formula I according to claim 1 comprising incorporating said one or more compounds of the formula I as components in a liquid-crystalline medium.

11. A liquid-crystalline medium comprising at least two mesogenic compounds, wherein at least one is a compound of the formula I according to claim 1.

12. An electro-optical liquid-crystal display containing a liquid-crystalline medium according to claim 11.

* * * * *